US006977511B2

(12) United States Patent
Patel et al.

(10) Patent No.: US 6,977,511 B2
(45) Date of Patent: Dec. 20, 2005

(54) SENSOR AND SENSOR ARRAY HAVING IMPROVED SELECTIVITY (75) Inventors: Sanjay V. Patel, San Diego, CA (US); Bernd Fruhberger, Encinitas, CA (US); Robert J. Warmack, Knoxville, TN (US); Todd E. Mlsna, Carlsbad, CA (US); David R. Baselt, San Diego, CA (US); Erno Klaassen, Sunnyvale, CA (US)

(73) Assignee: Xsilogy, Inc, San Diego, CA (US)

( * ) Notice: Subject to any disclaimer, the term of this patent is extended or adjusted under 35 U.S.C. 154(b) by 0 days.

(21) Appl. No.: 11/082,634

(22) Filed: Mar. 8, 2005

(65) Prior Publication Data
US 2005/0164285 A1 Jul. 28, 2005

Related U.S. Application Data (63) Continuation of application No. 10/177,133, filed on Jun. 20, 2002, now Pat. No. 6,864,692.

(51) Int. Cl.$^7$ .......................... G01R 27/26; H01G 5/16
(52) U.S. Cl. .................... 324/661; 73/23.31; 361/278
(58) Field of Search ............................... 324/658–664, 324/403.01, 403.02, 403.03, 403.04, 403.05, 324/403.06; 73/23.31, 31.02; 361/278, 280

(56) References Cited

U.S. PATENT DOCUMENTS

| 3,831,432 | A | * | 8/1974 | Cox .......................... 73/31.06 |
| 4,453,126 | A | * | 6/1984 | Volgyesi ...................... 422/88 |
| 4,542,640 | A | * | 9/1985 | Clifford ..................... 73/31.06 |
| 5,546,008 | A | * | 8/1996 | Sminchak et al. .......... 324/690 |
| 5,598,251 | A | * | 1/1997 | Parish et al. .................. 399/30 |
| 5,828,542 | A | * | 10/1998 | Riley et al. ................. 361/280 |

* cited by examiner

Primary Examiner—Anjan Deb
(74) Attorney, Agent, or Firm—Daniel M. Chambers; BioTechnology Law Group (57) ABSTRACT A sensor for determining the presence of an analyte is disclosed comprising a reactive layer disposed between a base plate and a movable plate. The reactive layer is configured to interact with an analyte effecting a change in capacitance between the base plate and movable plate. When the analyte has a polarity or overall Hildebrand solubility parameter that is similar to the reactive layer, the change in capacitance is caused by a swelling of the reactive layer as analyte is absorbed into the reactive layer. This results in a decrease in capacitance. When the analyte has a solubility parameter not near the reactive layer, the absorbed analyte causes the reactive layer's total polarity to increase, an effect that dominates swelling. This causes an increase in capacitance. A capacitive sensing circuit is included for measuring the change in capacitance which is indicative of the analyte exposed to the sensor.

15 Claims, 6 Drawing Sheets

SENSOR AND SENSOR ARRAY HAVING IMPROVED SELECTIVITY

RELATED APPLICATION

This application is a continuation of U.S. patent application Ser. No. 10/177,133, filed 20 Jun. 2002, and claims the benefit of and priority to the aforementioned patent application, which issued on 8 Mar. 2005 as U.S. patent No. 6,864,692. The entire disclosure of each of the aforementioned patent application and patent is considered part of the description of this application, and is hereby incorporated by reference in its entirety.

BACKGROUND OF THE INVENTION

1. Field of the Invention

The present invention is directed to chemical sensors. More particularly, the present invention is directed to chemical sensors and sensor arrays that employ a microcantilever to recognize chemical or biological agents exposed to the sensor.

2. Background Information

Various types of sensors have been used to detect the presence of chemical or biological agents. One class of sensor measures the swelling a common organic polymer undergoes as vapor molecules from the agent exposed to the sensor partition into the polymer. For example, agents having a Hildebrand solubility parameter similar to that of the polymer cause the polymer to swell. The degree of swelling can be measured to determine the concentration of a specific chemical or biological agent exposed to the sensor. However, the approach of measuring polymer swelling is not always useful when the agent has a solubility parameter that is far from that of the polymer because the polymer swelling is very small and thus hard to accurately measure.

Agent absorption into the polymer can be measured in a number of other ways as well. For example, one approach is to use a scanning force microscope (SFM) cantilever to measure increases in mass associated with absorption of the agent into the polymer. Other types of mass-sensitive resonant devices include the quartz-crystal microbalance, surface-acoustic-wave, and flexural-plate-wave resonator. In this type of sensor, an SFM-type cantilever is coated with a chemically or biologically active material. The cantilever is then driven into oscillation at a resonance frequency. As the agent molecules bind or absorb into the active layer on the cantilever, the mass of the vibrating cantilever increases. This increase can be measured as a shift in the cantilever vibration frequency or amplitude. One problem with these sensors is that the external circuitry required to drive the cantilever and measure the vibration can be cumbersome, expensive and power demanding.

Another approach for measuring polymer swelling is to observe the bending of a cantilever that is coated on one side with the polymer. As the polymer expands, the cantilever bends to accommodate the expansion. The difficulty with this approach is that a uniform polymer coating is difficult to apply and the polymer-cantilever interface can sometimes fail to statically maintain the stress differential.

Still another approach for measuring polymer swelling is to use partially conductive polymers to measure changes in conductivity of the polymer created as the polymer absorbs molecules from the agent. Partially conductive polymers can be created by incorporating carbon black particles or other conductive materials into the polymer. Upon incorporation of the carbon black particles, the normally non-conductive polymer becomes partially conductive. The composite is then deposited onto electrodes.

Exposure of the polymer/carbon composite to a chemical or biological agent causes the composite to swell. This swelling creates a drop in conductivity of the composite. Electronics connected to the electrodes can be used to measure the drop in conductivity.

This approach also suffers from problems. For example, the sensor can suffer from drift and variable sensitivity because the carbon particles may rearrange as the composite swells and contracts thus returning the polymer to a different nominal conductivity. Furthermore, the carbon particles themselves may absorb the chemical or biological agents thus extending the recovery time of the sensor. Additionally, all of the above approaches suffer from selectivity problems because the sensors measure only one factor affected by the analyte and two different analytes may affect the factor in similar manners.

Thus, there is a need for an improved sensor that can accurately identify a wide range of chemical or biological agents. There is also a need for an improved sensor that is durable and has a short recovery time. There is a further need for a sensor having improved selectivity.

SUMMARY OF THE INVENTION

These needs and others are satisfied by a sensor according to the present invention which comprises a conductive movable plate, a conductive base plate, a reactive layer disposed between the movable plate and base plate, and a capacitive sensing circuit. The reactive layer is configured to effect a change in capacitance between the movable plate and the base plate when the reactive layer is exposed to an analyte. The capacitive sensing circuit is configured for measuring the change in capacitance caused by response of the reactive layer to an analyte. The measured change in capacitance is indicative of the analyte.

Preferably, the reactive layer is configured to selectively and reversibly absorb the analyte. The reactive layer can be a polymer film, sol gel, or other suitable material. The analyte can be, among other things, chemical, biological, or radiation from a radioactive element.

The change in capacitance caused by the reactive layer reacting to the analyte can be due, at least in part, to a change in the dielectric properties of the reactive layer induced by the analyte being absorbed into the reactive layer. The change in capacitance can also be caused, in part, by a swelling of the reactive layer causing a change in the spacing between the movable plate and the base plate. Measuring changes in the capacitance caused by both dielectric changes in the reactive layer and changes in space between the movable plate and base plate provides additional information that can be used to ascertain the identity and concentration of an analyte in a mixture. For example, some analytes may have a dielectric function similar to that of the reactive layer. In that case, a reactive layer swelling would increase the capacitive gap and thus decrease the capacitance. Other analytes that have a high dielectric function might increase the capacitance by changing the dielectric properties of the reactive layer. Still others may have counterbalancing effects that result in a very low capacitance change. In any case, the response can be used in combination with data from other sensor types also exposed to the mixture to increase the selectivity for particular analytes.

A readout circuit for displaying the measured change in capacitance can also be included. The sensor can also include a transmitter for transmitting the measured change in capacitance to a receiver positioned at a location remote from the sensor and a receiver for receiving instructions from the remote location.

In another embodiment of the invention, a sensor array can be configured using a plurality of sensors, each having a different reactive layer. Pattern recognition software or neural networks can be used with the sensor array to increase sensitivity and more accurately determine the presence of particular analytes.

DETAILED DESCRIPTION OF A PREFERRED EMBODIMENT OF THE INVENTION

In accordance with the present invention, a sensor is described that provides distinct advantages when compared to those of the prior art. The invention can best be understood with reference to the accompanying drawing figures.

Figure 1:
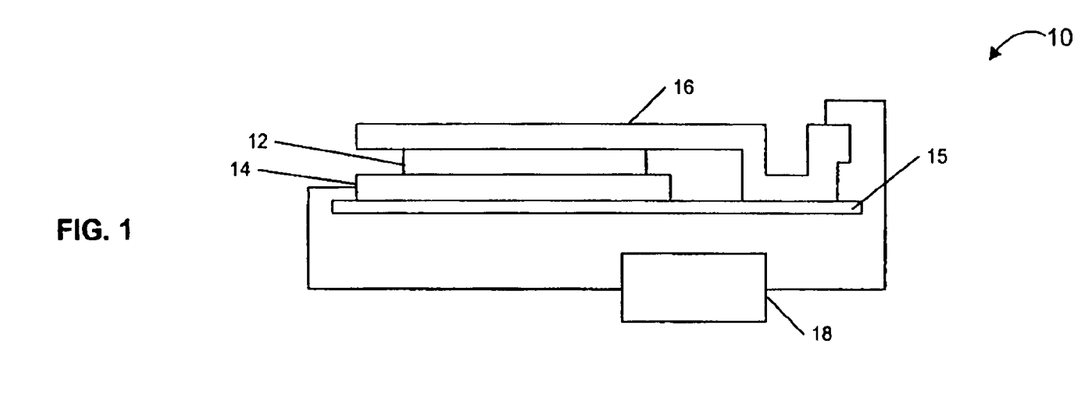
FIG. 1 is a side view of a sensor according to the present invention.
Figure 2:
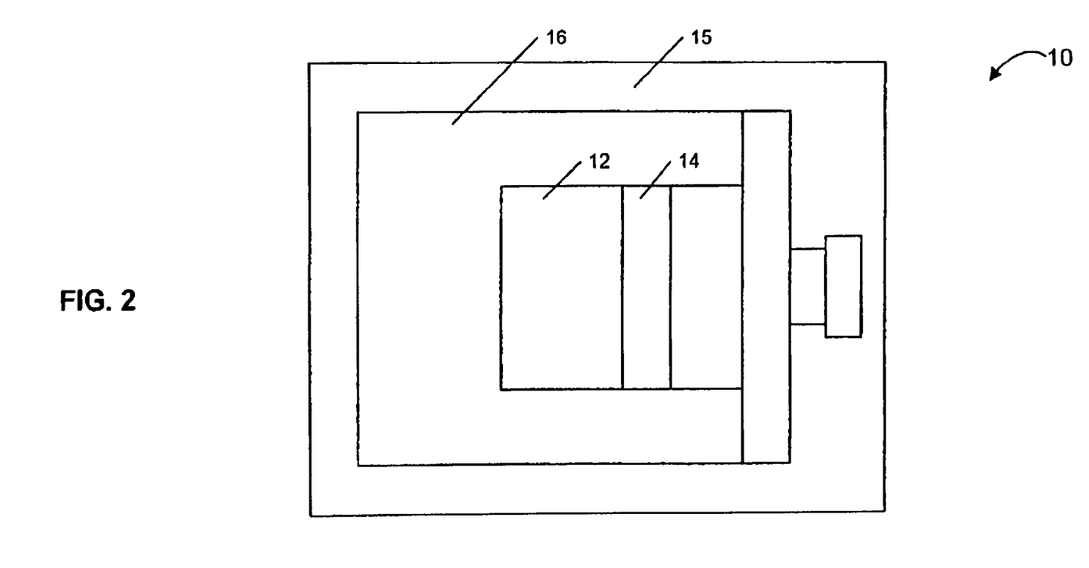
FIG. 2 is a top view of the sensor shown in FIG. 1.

Referring now to the drawings, a sensor according to the present invention is generally designated by reference numeral 10 in FIGS. 1 and 2. The sensor 10 comprises a reactive layer 12 disposed between a base plate 14 and a movable plate, which in this embodiment is shown as cantilever 16. A capacitive sensing circuit 18 is connected between the base plate 14 and cantilever 16 for detecting a change in capacitance ($\Delta C_{capacitance}$) therebetween. Preferably, the sensor 10 comprises a MEMS (micro-electromechanical systems) device with the base plate 14 and cantilever 16 attached to a substrate 15.

Preferably, the reactive layer 12 comprises a polymer material. The reactive layer 12 can comprise one of any number of materials specifically selected for reacting to certain analytes. For example, the reactive layer 12 can comprise a polymer film for detecting, among other things, volatile organic compounds or chemical warfare agents. Polymers having a polarity or dielectric function similar to the polarity of the analyte will swell significantly when exposed to the analyte. Conversely, if the dielectric function of the analyte is high in comparison to the polymer, it will cause an increase in the capacitance due to dielectric changes in the polymer as the analyte is absorbed into the polymer. Sample reactive layer 12 polymer film materials can include: Polyethylene (PE), Polyisobutylene (PIB), Polystyrene (PS), Polypropylene (PP), Polyether urethane (PEUT), Polycarbonate (PC), Ethyl Cellulose (EC), Polydimethyl siloxane (PDMS), Silicone Epoxy, Polymethyl methacrylate (PMMA), Polyamides (PAM), Polyvinyl chloride (PVC), Cellulose Acetate, Poly urethane (PU), Polyvinyl acetate (PVAC), Polyimides (PI), Siloxanefluoroalcohol (SXFA), Polyethylene-co-vinylacetate (PEVA), or any other suitable polymer film material. The reactive layer 12 can also comprise a mixture of polymer materials such as Polydimethylsiloxane (PDMS) and Polyethyleneimine (PEI) in a 5:1 ratio.

Alternatively, the reactive layer 12 can comprise a sol gel for detecting emission gases, such as carbon dioxide, carbon monoxide, sulfur dioxide, and nitrogen oxides. Suitable sol gel materials can include alkylpolydimethoxysilanes, aminoalkypolydimethoxysilanes, aminoalkylpolytrimethoxysilanes, and dimethylaminoalkylpolyoxysilanes, tetraethylorthosilicate or other suitable sol gel material. Aerogels, zeolites, and silicalites may also be suitable materials for use as the reactive layer 12.

Preferably, the base plate 14 comprises a conductive material such as doped polysilicon for MEMS fabrication. The cantilever 16 also comprises a conductive material such as polysilicon, single crystal silicon, or a metal such as nickel, aluminum, etc. Alternatively, the cantilever 16 can comprise a dielectric mechanical layer with a conductive layer on one side. The cantilever 16 is perforated to allow access of the analyte to the reactive layer 12. The cantilever 16 should be strong and resilient enough to withstand flexing caused by swelling of the reactive layer 12.

Preferably, the reactive layer 12 is a polymer, which is deposited through or around the cantilever 16 onto the base plate 14 in atmosphere of solvent to ensure a uniform reactive layer 12. This can be done by dissolving the reactive layer material in a solvent, coating the base plate 14 with the reactive layer material/solvent solution, and baking the solvent out of the solution leaving an even coat of reactive layer material on the base plate 14. The base plate 14 can be pre-treated to promote adhesion. For example, the base plate 14 can be treated with an acid or base or silane reagent to insure compatibility between the reactive layer material solvent and the base plate 14.

Figure 3:
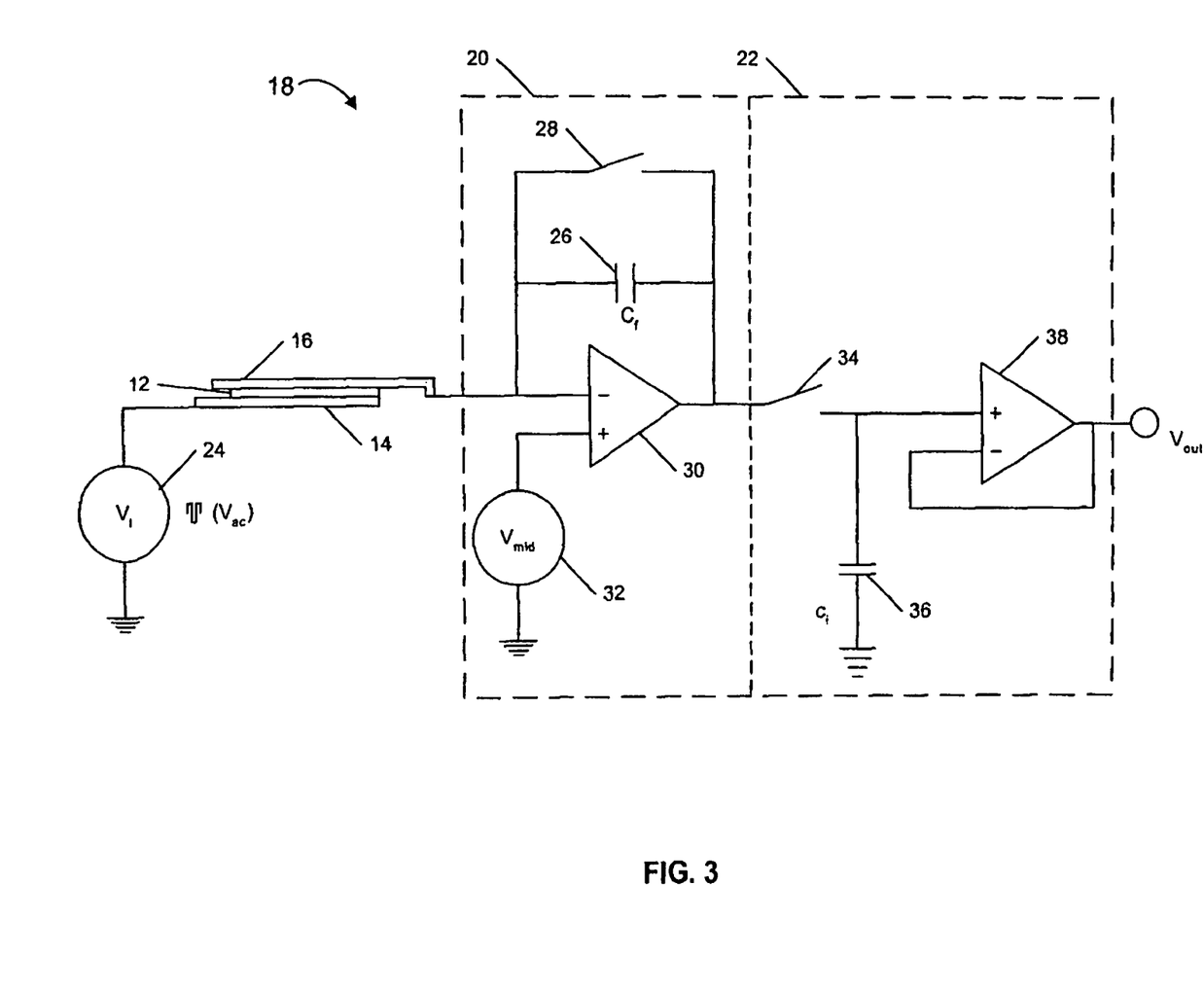
FIG. 3 is a schematic diagram of the capacitive sensing circuit shown in FIG. 1.

FIG. 3 illustrates one embodiment of a capacitive sensing circuit 18 according to the present invention. The capacitive sensing circuit 18 includes a gain stage 20 and a sample-and-hold stage 22. A grounded input voltage source (Vi) 24 is connected to the base plate 14 and the gain stage 20 is connected to the cantilever 16. Preferably, the input voltage source (Vi) 24 supplies a square wave voltage pulse (Vac). With the appropriate driving waveforms, the output voltage change $\Delta V_{out}$ is given by:

$$\Delta V_{out} = \Delta C_{cantilever} * V_{ac}(\text{peak-peak})/C_f$$

The gain stage 20 comprises feedback capacitor ($C_f$) 26, reset switch 28, and operational amplifier 30 all connected in parallel. A signal indicating the capacitance between the base plate 14 and cantilever 16 is input into the operational amplifier 30. Reset switch 28 is closed to reset the feedback capacitor ($C_f$) 26 input to the operational amplifier 30. When the reset switch 28 is opened, a signal from the feedback capacitor ($C_f$) 26 is restored to the input of operational amplifier 30.

The operational amplifier 30 is connected to a voltage source ($V_{mid}$) 32, which is an independently grounded source. Preferably, voltage source ($V_{mid}$) 32 is a DC voltage source. The existence of a grounded input voltage source ($V_i$) 24 on the base plate 14 and a virtual ground produced by the feedback action of feedback capacitor ($C_f$) 26 and operational amplifier 30 on the cantilever 16 eliminates the effects of stray capacitance on both the base plate 14 and cantilever 16.

The value of feedback capacitor ($C_f$) 26 is digitally adjustable. The system controller can therefore change the gain of the gain stage 20 in two ways: by changing the feedback capacitor ($C_f$) 26 or by adjusting the amplitude of the input voltage source ($V_i$) 24. This allows tradeoff between high sensitivity (high gain) and large dynamic range (low gain).

The sample-and-hold stage 22 is used to create a DC output voltage from the AC signal and the output of the gain stage 20. The sample-and-hold stage 22 comprises switch 34, input capacitor (Ci) 36, and amplifier 38. When switch 34 is closed, the voltage at the input of the sample-and-hold stage 22 is sampled. When switch 34 is open, the sample-and-hold stage 22 holds the voltage of the previous sample until the next sample is taken. A timing circuit (not shown) can be included to control the operation of reset switch 28 and switch 34.

In operation, the sensor 10 can determine the presence of a particular analyte by measuring a change in capacitance of the sensor 10 caused by exposure to the analyte. The change in capacitance can be caused by a change in the dielectric properties of the reactive layer 12 caused by changing the bulk dielectric constant of the reactive layer 12, due to absorption of the analyte into the reactive layer 12, a change in the distance between the base plate 14 and the cantilever 16 caused by a swelling of the reactive layer 12 due to absorption of the analyte into the reactive layer 12, or a combination of both of these factors.

When the analyte has a polarity or overall Hildebrand solubility parameter that is similar to the reactive layer 12, the reactive layer 12 swells and lifts the cantilever 16. Hydrocarbon volatile organic chemicals (VOCs), most aromatic VOCs, and reactive layers 12 that absorb these hydrocarbons have low dielectric constants. Thus, the resulting measured increase in $V_{out}$, caused by a decrease in capacitance, is primarily due to swelling of the reactive layer 12. If the analyte has a solubility parameter greater than the reactive layer 12, the absorbed analyte causes the reactive layer's 12 total polarity to increase, an effect that dominates the swelling effect, resulting in a measured decrease in $V_{out}$, caused by an increase in $\Delta C_{cantilever}$. Thus, a sensor 10 according to the present invention can accurately sense both analytes that do not cause significant swelling in the reactive layer 12, as well as those that do.

Figure 4:
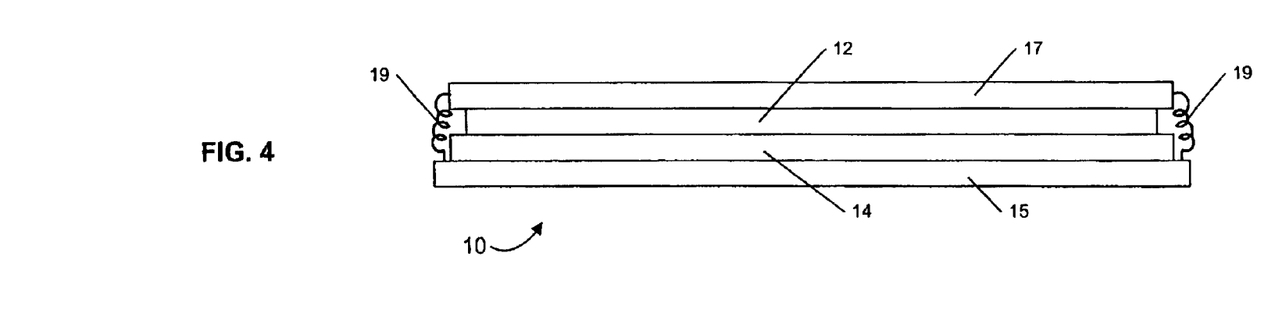
FIG. 4 is side view of an alternative embodiment of a sensor according to the present invention.
Figure 5:
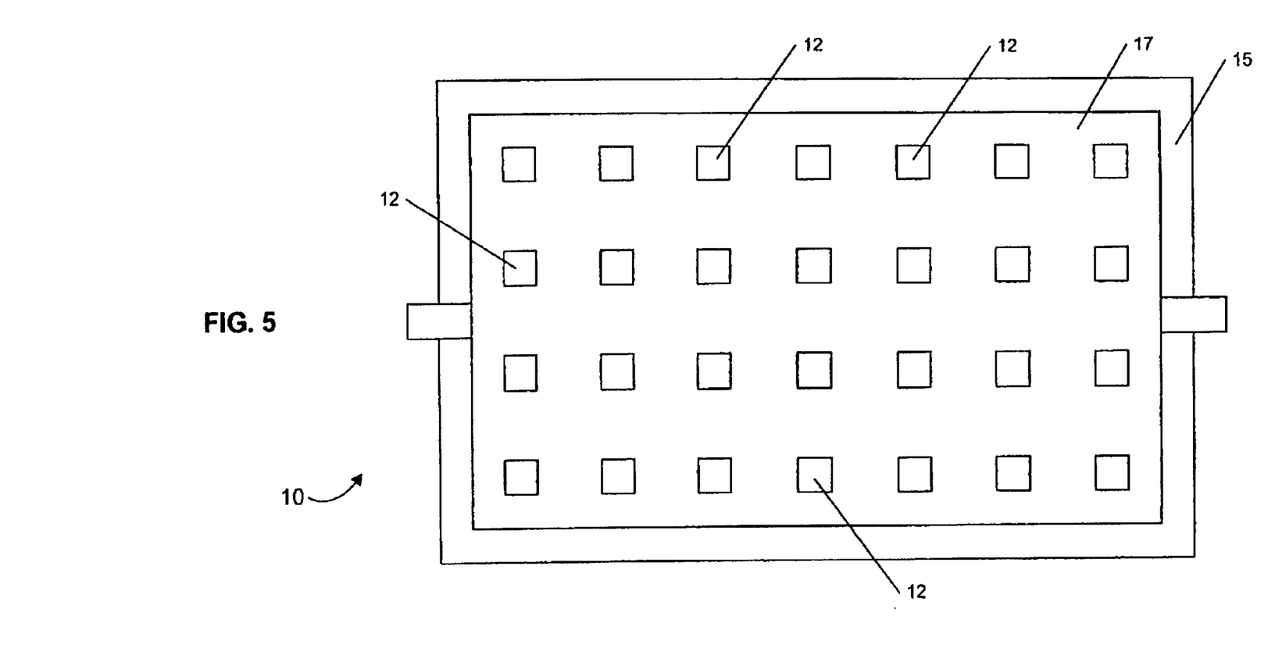
FIG. 5 is a top view of the sensor shown in FIG. 4.

FIGS. 4 and 5 illustrate one alternative embodiment of an improved sensor according to the present invention. In this embodiment, the cantilever 16 of sensor 10 is replaced with a tethered movable plate 17. The tethered movable plate 17 operates in essentially the same manner as cantilever 16. Preferably, tethered movable plate 17 comprises a conductive material such as polysilicon, single crystal silicon, or a metal such as nickel, aluminum, etc. Alternatively, tethered movable plate 17 can comprise a dielectric mechanical layer with a conductive layer on one side. Tethered movable plate 17 can be perforated to allow access of the analyte to the reactive layer 12.

Tethered movable plate 17 is movably attached to the substrate 15 such as with flexible springs 19 at each end. The flexible springs 19 allow the tethered movable plate 17 to move up or down with respect to the base plate 14 to accommodate reactive layer 12 swelling or contracting.

Figure 6:
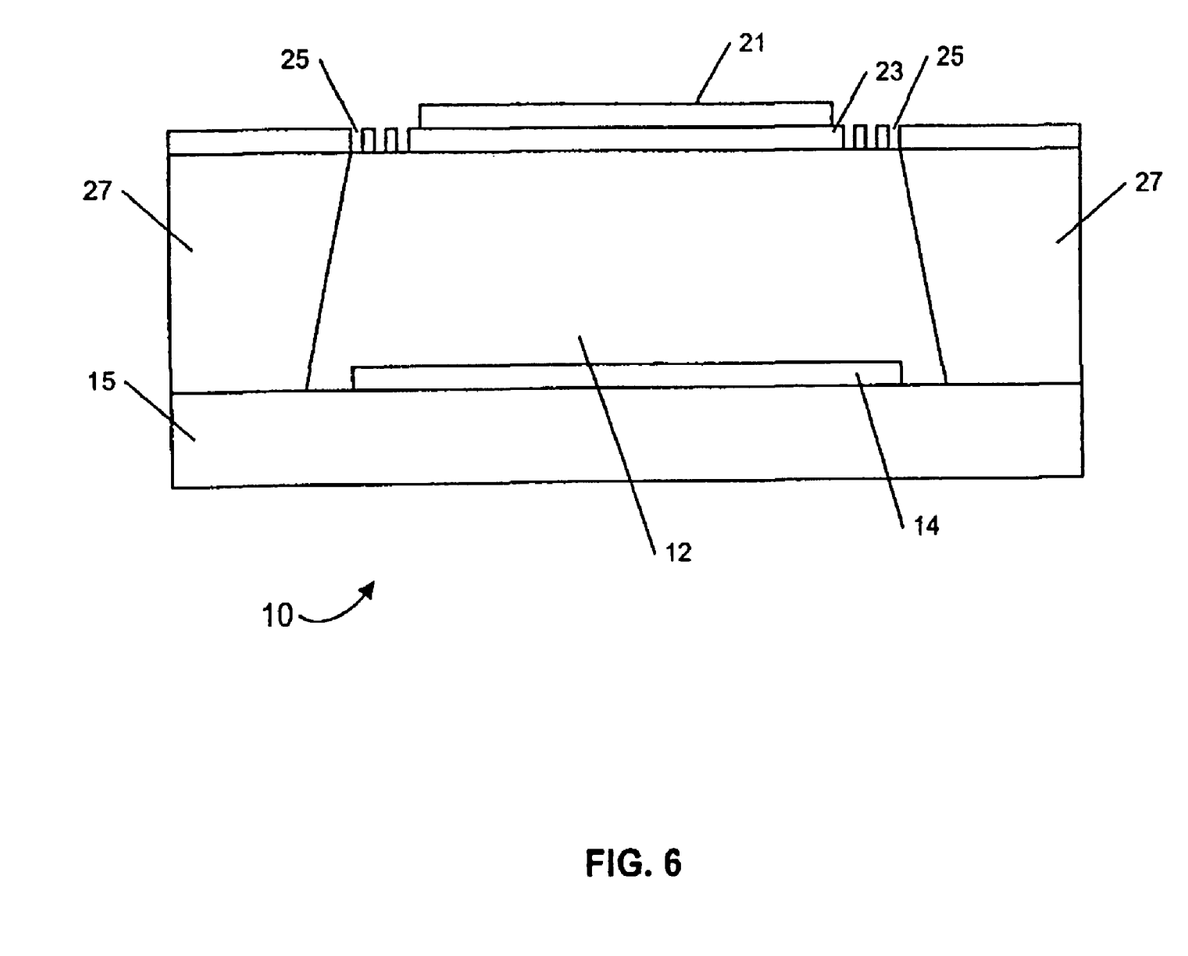
FIG. 6 is a side view of another alternative embodiment of a sensor according to the present invention.

Alternatively, the tethered movable plate can comprise a top electrode 21 placed on a flexible membrane 23 as shown in FIG. 6. The reactive layer 12 is placed between the membrane 23 and base plate 14. The membrane 23 can be made of an insulator such as silicon dioxide or silicon nitride. The top electrode 21 can be made of a metal or other conductive material. Alternatively, the membrane 23 can be made of a flexible polysilicon or metal material eliminating the need for a separate top electrode. Preferably, the membrane includes etched through holes 25 for allowing the reactive layer 12 to be injected between the membrane 23 and base plate 14. An insulating rim 27 can also be included for providing a lateral boundary for the reactive layer 12.

Figure 7:
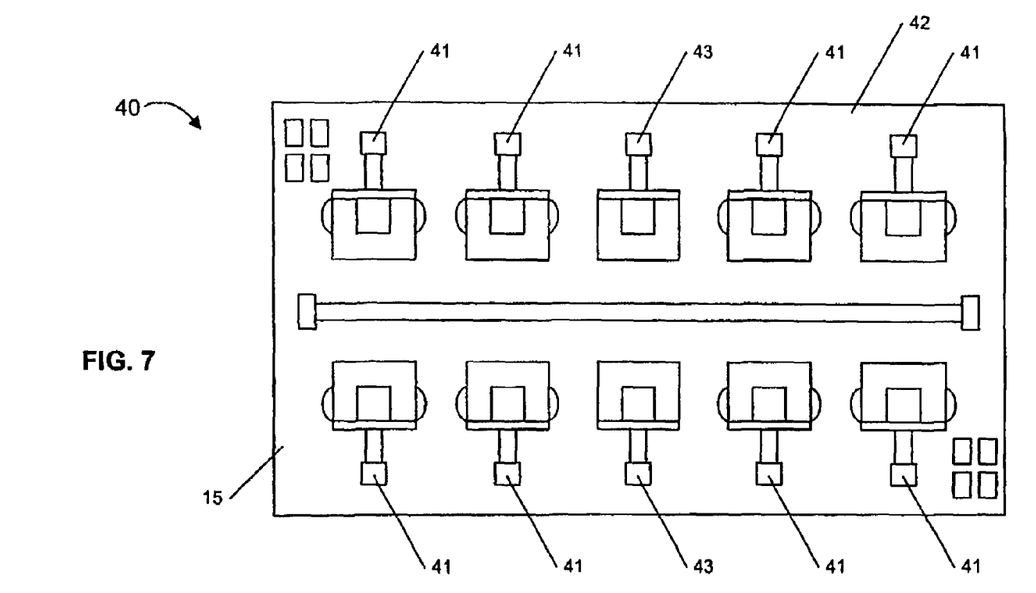
FIG. 7 is a top view of a sensor array according to the present invention.
Figure 8:
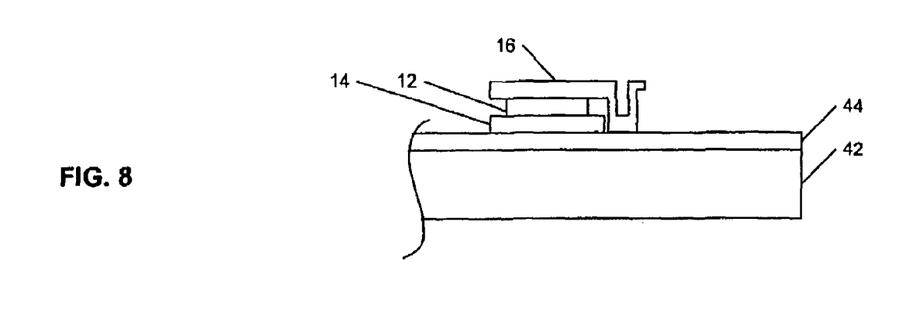
FIG. 8 is a cross-sectional side view of the sensor array of FIG. 4.

In another embodiment of the invention, shown in FIGS. 7 and 8, a plurality of sensors 10 are arranged in a sensor array 40 on a silicon chip 42. An insulative layer 44 is included between the silicon chip 42 and sensors 10 for electrically insulating the sensors 10 from the silicon chip 42. Each sensor 10 can be loaded with a different reactive layer 12 each with a different Hildebrand solubility parameter. As such, each sensor 10 will react differently when exposed to an analyte creating a unique response pattern. The response pattern can be used to discriminate between a variety of analytes. Pattern recognition algorithms and/or neural networks can be used with the sensor array 40 to increase selectivity by matching sensor 10 reaction patterns with known responses to certain analytes. For example, "The Unscrambler"™ distributed by Camo, Inc. provides a software program capable of principle components analysis.

In the embodiment shown in FIGS. 7 and 8, ten sensors 10 are arranged on a single silicon chip 42. The silicon chip 42 is 2 by 5 mm and is configured to hold ten sensors having 300 by 500 $\mu$m cantilevers 16. Eight of the sensors 41 include reactive layers 12 between their base plate 14 and cantilever 16 and two do not, leaving them to be used as possible reference sensors 43. A typical capacitance of one of the reference sensors 43 is about ⅓ of a picofarad. The capacitive sensing circuit can measure changes in capacitance of a few hundreds of attofarads. For changes of capacitance due to reactive layer 12 swelling, this can correspond to a cantilever 16 deflection of a few nanometers.

Figure 9:
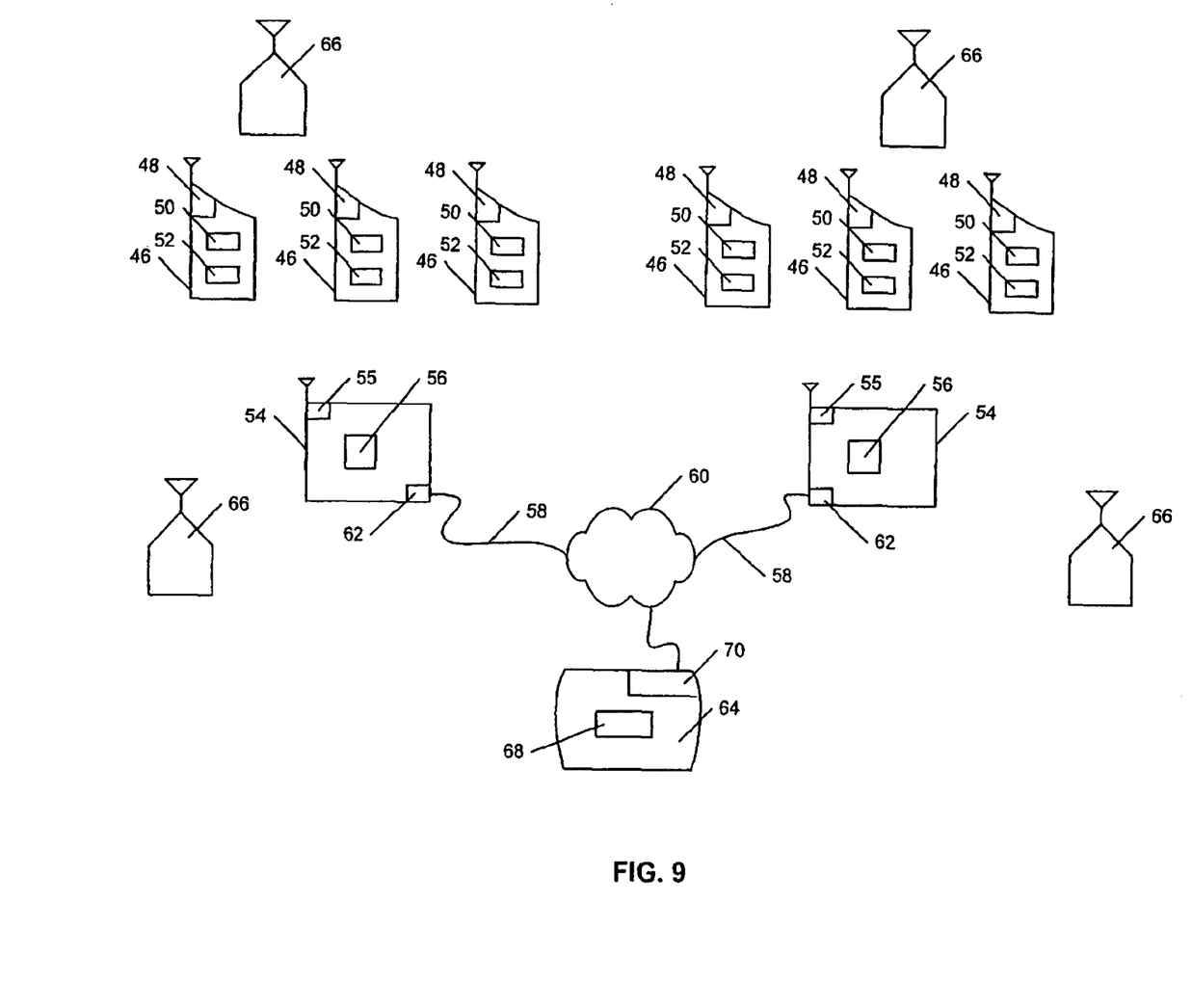
FIG. 9 is a block diagram of a wireless sensor according to the present invention.

A wireless sensor 46 according to the present invention is shown in FIG. 9. A plurality of wireless sensors 46 can be used together in a sensor network. The wireless sensor 46 includes a wireless transceiver 48, a processor 50, and memory 52. The processor 50 may be an embedded processor. While it may be formed as a conventional microprocessor, with all of its attendant functionality, it may also be a processor more particularly adapted to the tasks required of the wireless sensor 46 and the communication and processing of sensed data. One such processor may be an ARM processor. Such a system is a RISC (reduced instructions set computer).

The transceiver 48 is configured to communicate with a node 54. The node 54 may include a transceiver 55, and a processor 56. The processor 56 may be of any type consistent with the functionalities required, though the structures and functionalities described in connection with the processor 50 of the wireless sensor 46 may be utilized for the node 54. A network connection 58 serves to interconnect node 54 to the net 60 via connector 62. The node 54 serves to perform various functions, such as: processing of data received from one or more wireless sensor 48, performing data analysis on information received from the wireless sensor 46 or end user machine 64 to provide control or information to an actuator 66, to communicate with the end user machine 64, to provide redundancy to the system and to provide the possibility of direct access via a web browser over the Internet to access the node 54, and to thereby obtain information or control over or from the wireless sensors 48 or an actuator 66.

The end user machine 64 includes a processor 68 that can be coupled to the net 60 by network connection 70. Network connection 60 provides for communication between processor 68, running application software 72 and wireless sensors 46 over the net 60. In this manner, the wireless sensor 46 sends data to and receives instruction from node 54 and an end user machine 64 via the net 60.

While the particular systems and methods for sensing herein shown and described in detail are fully capable of attaining the above described objects of the this invention, it is to be understood that the description and drawings presented herein represent one embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A sensor array for sensing an airborne analyte, the sensor array comprising at least a first sensor and a second sensor, wherein at least the first sensor comprises:
   a first conductive plate, which first conductive plate serves as a base plate;
   a second conductive plate disposed in spaced relation to and in electrical communication with the first conductive plate, wherein at least a portion of the second conductive plate is moveable in relation to the first conductive plate;
   a reactive layer disposed between at least a portion of the second conductive plate and the first conductive plate, the reactive layer being comprised of a polymer film comprised of at least one polymer species and configured to effect a change in capacitance between the second conductive plate and the first conductive plate when the reactive layer is exposed to the analyte; and
   a capacitance sensing circuit for detecting a change in capacitance between the first conductive plate and the second conductive plate indicative of the presence of the analyte.

2. A sensor array according to claim 1 wherein the reactive layer of the first sensor is configured to selectively and reversibly absorb the analyte.

3. A sensor array according to claim 1 wherein the change in capacitance in the first sensor is due at least in part to a change in dielectric properties of the reactive layer caused by the analyte being absorbed into the reactive layer.

4. A sensor array according to claim 1 wherein the change in capacitance in the first sensor is due at least in part to a swelling of the reactive layer caused by the analyte being absorbed into the reactive layer.

5. A sensor array according to claim 1 wherein the reactive layer of the first sensor comprises a sol gel.

6. A sensor array according to claim 1 further comprising a readout circuit for displaying results from the sensor array.

7. A sensor array according to claim 1 further comprising a transmitter for transmitting data from the sensor array to a receiver positioned at a location remote from the sensor.

8. A sensor array according to claim 1 wherein the second conductive plate of the first sensor comprises a structure selected from the group consisting of a cantilever, a tethered moveable plate, and a flexible membrane.

9. A sensor array according to claim 8 wherein the second conductive plate of the first sensor is perforated to facilitate access of the analyte to the reactive layer.

10. A sensor array according to claim 1 wherein the analyte is selected from the group consisting of a volatile organic compound, a chemical warfare agent, and a biological warfare agent.

11. A sensor array according to claim 1 wherein the analyte is an emission gas.

12. A sensor array according to claim 1 wherein the polymer species of the first sensor that comprises the polymer film is a compound selected from the group consisting of polycarbonate, polyethylene, polyisobutylene, polypropylene, polystyrene, polyether urethane, ethyl cellulose, polydimethyl siloxane, silicone epoxy, polymethyl methacrylate, a polyamide, polyvinyl chloride, cellulose acteate, polyurethane, polyvinyl acetate, a polyimide, siloxanefluoroalcohol, and polyethylene-co-vinylacetate.

13. A sensor array according to claim 1 wherein each of the sensors comprises:
   a first conductive plate, which first conductive plate serves as a base plate;
   a second conductive plate disposed in spaced relation to and in electrical communication with the first conductive plate, wherein at least a portion of the second conductive plate is moveable in relation to the first conductive plate;
   a reactive layer disposed between at least a portion of the second conductive plate and the first conductive plate, the reactive layer being comprised of a polymer film comprised of at least one polymer species and configured to effect a change in capacitance between the second conductive plate and the first conductive plate when the reactive layer is exposed to the analyte; and
   a capacitance sensing circuit for detecting a change in capacitance between the first conductive plate and the second conductive plate indicative of the presence of the analyte.

14. A sensor array according to claim 13 wherein the reactive layer of each sensor differs from the reactive layers of the other sensors.

15. A sensor array according to claim 13 capable of detecting a plurality of airborne analytes.

* * * * *